United States Patent [19]
Boon et al.

[11] Patent Number: 5,866,581
[45] Date of Patent: *Feb. 2, 1999

[54] PENCICLOVIR FOR THE TREATMENT OF POST THERAPEUTIC NEURALGIA

[75] Inventors: Ronald James Boon, Dorking; David Ronald John Griffin, Bishop's Stortford, both of England

[73] Assignee: SmithKline Beecham p.l.c., Brentford, England

[*] Notice: This patent issued on a continued prosecution application filed under 37 CFR 1.53(d), and is subject to the twenty year patent term provisions of 35 U.S.C. 154(a)(2).

[21] Appl. No.: 624,466
[22] PCT Filed: Oct. 4, 1994
[86] PCT No.: PCT/GB94/02156
   § 371 Date: Jun. 20, 1996
   § 102(e) Date: Jun. 20, 1996
[87] PCT Pub. No.: WO95/09632
   PCT Pub. Date: Apr. 13, 1995

[30] Foreign Application Priority Data

Oct. 5, 1993 [GB] United Kingdom .................. 9320485
   Oct. 14, 1993 [GB] United Kingdom .................. 9321255

[51] Int. Cl.$^6$ .................................................. A61K 31/52
[52] U.S. Cl. ............................................................ 514/262
[58] Field of Search ............................................ 514/262

[56] References Cited

FOREIGN PATENT DOCUMENTS 0 141 927  5/1985  European Pat. Off. .
   0 182 024  5/1986  European Pat. Off. .

OTHER PUBLICATIONS

Poster from ICAAC, Oct. 11–14, 1992.
Poster from ICAAC, Oct. 17–20, 1993.
Wood et al., Scand. J. Infect. Dis., 23(80), pp. 53–61, 1991.
Robertson et al., Br. Med. Bull., 46(1), pp. 113–123, 1990.
Klenerman et al., Biomed. Pharmacother., 44(9), pp. 455–459, 1990.
Schmader et al., J. Gen. Intern. Med., 4(2), pp. 83–89, 1989.
McKendrick, et al., British Medical Journal, vol. 293, pp. 1529–1532 (1986).
Huff, et al., The American Journal of Medicine, vol. 85 (Suppl 2A), pp. 84–89, (1988).
Morton, et al., The New Zealand Medical Journal, vol. 102, No. 863, pp. 93–95, (1989).
Huff, et al., Journal of Medical Virology, Supplement 1, pp. 93–96 (1993).
Wood, et al., The New England Journal of Medicine, vol. 330, pp. 896–900, (1994).
Beutner and The International Valaciclovir Zoster Study Group, Abstract (1994).
Wood, et al., Infection 15, Suppl. 1, pp. S9–S13, (1987).
Harding, Journal of Medical Virology, Suppl. 1, pp. 97–101 (1993).
Crooks, et al., Scand J. Infect, Suppl. 78, pp. 64–70 (1991).
McKendrick, et al., British Medical Journal, 298:431 (1988).

*Primary Examiner*—Phyllis G. Spivack
*Attorney, Agent, or Firm*—Dara L. Dinner; Stephen Venetianer

[57] ABSTRACT

A method for the treatment of PHN in mammals, including humans, which method comprises administering an effective amount of a compound of formula (A), or a pharmaceutically acceptable salt thereof.

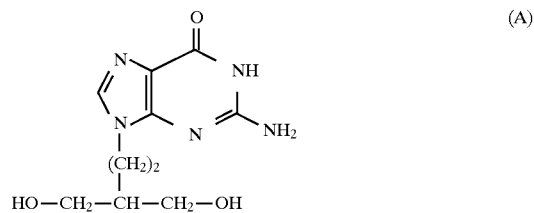

21 Claims, 2 Drawing Sheets

Figure 1A. - Kaplan-Meier Plots of Time to Loss of Postherpetic Neuralgia, All Patients

PENCICLOVIR FOR THE TREATMENT OF POST THERAPEUTIC NEURALGIA

This application is a 371 of PCT/GB94/02156 filed Oct. 4, 1994.

FIELD OF THE INVENTION

This invention relates to treatment of post-herpetic neuralgia, and to the use of compounds in the preparation of a medicament for use in the treatment of such conditions.

When used herein, 'treatment' includes prophylaxis as appropriate.

BACKGROUND OF THE INVENTION

EP-A-141927 (Beecham Group p.l.c.) discloses penciclovir, the compound of formula (A):

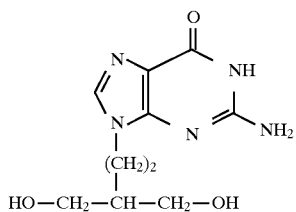

and salts, phosphate esters and acyl derivatives thereof, as antiviral agents. The sodium salt hydrate of penciclovir is disclosed in EP-A-216459 (Beecham Group p.l.c.). Penciclovir and its antiviral activity is also disclosed in Abstract P.V11-5 p. 193 of 'Abstracts of 14th Int. Congress of Microbiology', Manchester, England 7–13 Sep. 1986 (Boyd et. al.).

Orally active bioprecursors of the compound of formula (A) are of formula (B):

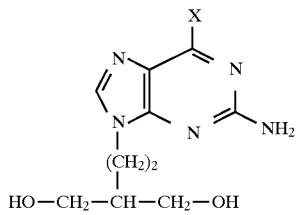

and salts and derivatives thereof as defined under formula (A); wherein X is $C_{1-6}$ alkoxy, $NH_2$ or hydrogen. The compounds of formula (B) wherein X is $C_{1-6}$ alkoxy or $NH_2$ are disclosed in EP-A-141927 and the compounds of formula (B) wherein X is hydrogen, disclosed in EP-A-182024 (Beecham Group p.l.c.) are preferred prodrugs. A particularly preferred example of a compound of formula (B) is that wherein X is hydrogen and wherein the two OH groups are in the form of the acetyl derivative, described in Example 2 of EP-A-1 82024, hereinafter referred to as famciclovir.

The compounds of formulae (A) and (B) and salts and derivatives thereof have been described as useful in the treatment of infections caused by herpesviruses, such as herpes simplex type 1, herpes simplex type 2, varicella-zoster and Epstein-Barr viruses.

Post-herpetic neuralgia (PHN) is by far the most common complication of herpes zoster infection and is one of the most intractable pain disorders (Strommen et al, Pharmacotherapy. 1988;8:52–68). Patients who develop PHN suffer from a debilitating and often intractable pain which can persist for months or even years. Although rare in patients under 50 years of age, the frequency of PHN rises steeply with increasing age.

There is currently no proven therapy for preventing PHN. The pain is due to injury of the nervous system and therefore seldom responds to analgesia used to treat pain associated with tissue damage. Hence, there is a need for therapy which alleviates or shortens the duration of post-herpetic neuralgia.

SUMMARY OF THE INVENTION

It has now been discovered that the above compounds are particularly effective in reducing the duration of PHN when given to the patient during the acute infection.

Accordingly, the present invention provides a method of treatment of PHN in humans, which method comprises the administration to the human in need of such treatment, an effective amount of a compound of formula (A):

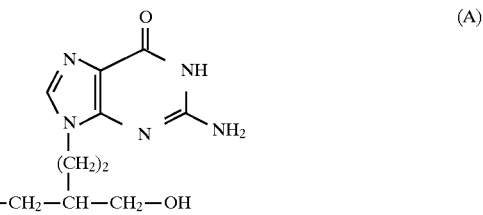

or a bioprecursor, or a pharmaceutically acceptable salt, phosphate ester and/or acyl derivative of either of the foregoing.

DETAILED DESCRIPTION OF THE INVENTION

Figure 1:
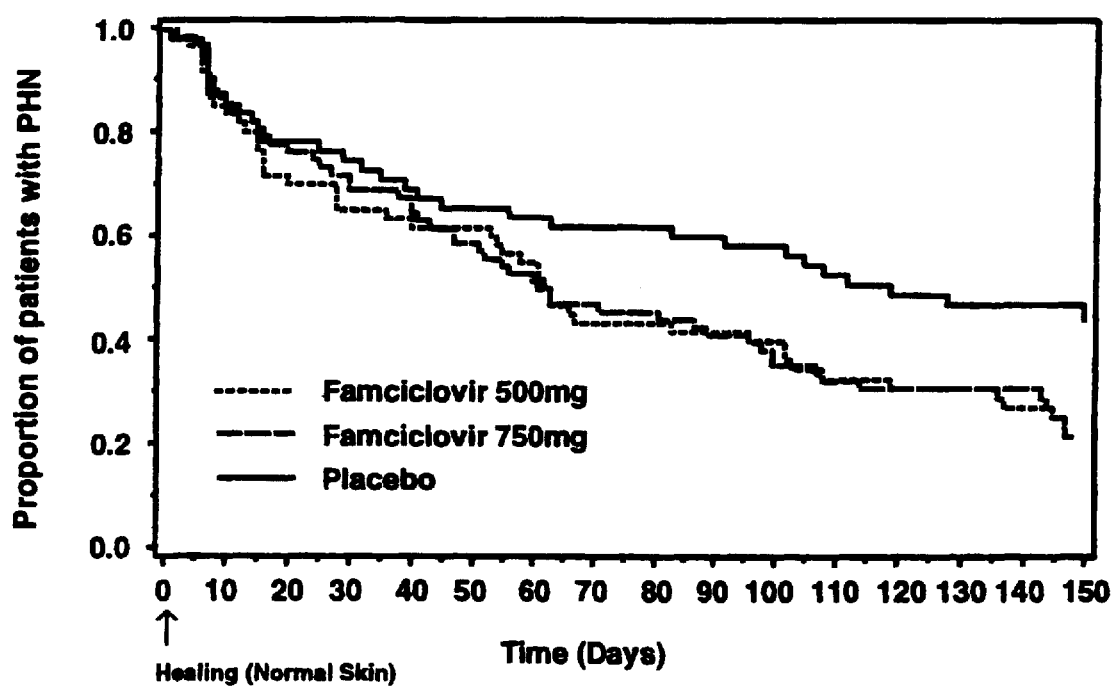
FIG. 1 shows a Kaplan-Meier Plot of Time to Loss of Postherpetic Neuralgia (PHN) in a Patient Population in which famciclovir doses significantly reduce the duration of PHN.
Figure 2:
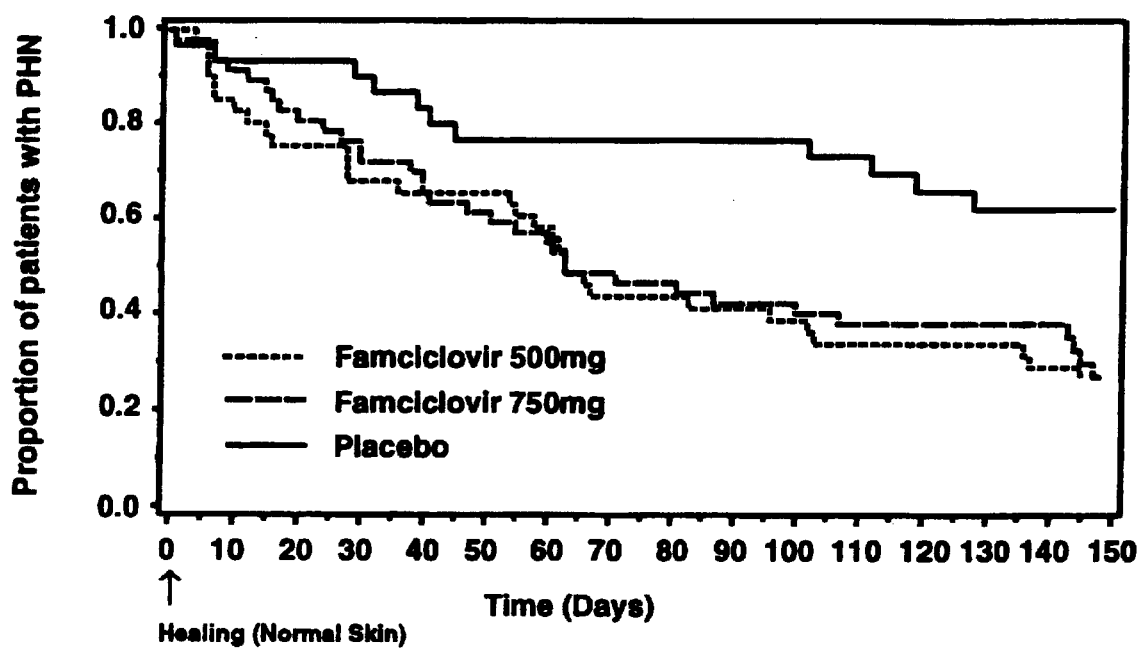
FIG. 2 shows a Kaplan-Meier Plot of Time to Loss of Postherpetic Neuralgia (PHN) in a Patient Population over >50 years of age in which famciclovir resolved PHN 2.6 times faster than in placebo treated patients.

The term 'acyl derivative' is used herein to include any derivative of the compounds of formula (A) in which one or more acyl groups are present. Such derivatives are included as bioprecursors of the compounds of formula (A) in addition to those derivatives which are per se biologically active.

The compound of formula (A) may be in one of the forms disclosed in EP-A-216459 (Beecham Group p.l.c.).

Examples of bioprecursors, pharmaceutically acceptable salts and derivatives are as described in the aforementioned European Patent references, the subject matter of which are incorporated herein by reference.

A particular compound of formula (B) of interest is 9-(4-acetoxy-3-acetoxymethylbut-1-yl)-2-aminopurine, known as famciclovir (FCV), the well-absorbed oral form of penciclovir (PCV).

The compound of formula (A), bioprecursors, salts and derivatives may be prepared as described in the aforementioned European Patent references.

The compound, in particular, famciclovir, may be administered by the oral route to humans and may be compounded in the form of syrup, tablets or capsule. When in the form of a tablet, any pharmaceutical carrier suitable for formulating such solid compositions may be used, for example magnesium stearate, starch, lactose, glucose, rice, flour and chalk. The compound may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. Sustained release formulations, for example tablets containing an enteric coating, are also envisaged.

For parenteral administration, fluid unit dose forms are prepared containing the compound and a sterile vehicle. The compound depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

Preferred parenteral formulations include aqueous formulations using sterile water or normal saline, at a pH of around 7.4 or greater, in particular, containing penciclovir sodium salt hydrate.

As is common practice, the compositions will usually be accompanied by written or printed directions for use in the medical treatment concerned.

An amount effective to treat the virus infection depends on the nature and severity of the infection and the weight of the mammal.

A suitable dosage unit might contain from 50 mg to 1 g of active ingredient, for example 100 to 500 mg. Such doses may be administered 1 to 4 times a day or more usually 2 or 3 times a day. The effective dose of compound will, in general, be in the range of from 0.2 to 40 mg per kilogram of body weight per day or, more usually, 10 to 20 mg/kg per day in the case of famciclovir, the dosage unit would be 250 mg, 500 mg or 750 mg, preferably 250 mg or 500 mg.

The treatment is preferably carried out as soon as possible after symptoms appear usually within 72 hours, preferably within 48 hours of rash onset.

The treatment period is usually 7 days.

The treatment is particularly effective in the case of patients of greater than 50 years of age, and efficacy would be expected to be demonstrated further in patients greater than 60 years of age, especially patients of greater than 70 years of age.

The present invention also provides the use of a compound of formula (A) or a bioprecursor, or a pharmaceutically acceptable salt, phosphate ester and/or acyl derivative of either of the foregoing, in the preparation of a medicament for use in the treatment of PHN. Such treatment may be carried out in the manner as hereinbefore described.

The present invention further provides a pharmaceutical composition for use in the treatment of PHN, which comprises an effective amount of a compound of formula (A) or a bioprecursor, or a pharmaceutically acceptable salt, phosphate ester and/or acyl derivative of either of the foregoing, and a pharmaceutically acceptable carrier. Such compositions may be prepared in the manner as hereinafter described.

The compound of formula (A) and its prodrugs show a synergistic antiviral effect in conjunction with interferons; and treatment using combination products comprising these two components for sequential or concomitant administration, by the same or different routes, are therefore within the ambit of the present invention. Such products are described in EP-A-271270 (Beecham Group p.l.c.).

The following clinical data and paper for publication, entitled 'Famciclovir for the treatment of Acute Disease and Postherpetic Neuralgia' illustrate the invention.(ref.— Tyring et al Abstract 1540 of the 32nd Interscience Conference on Antimicrobial Agents and Chemotherapy. New Orleans. American Society of Microbiology, 1993.)

Clinical Data

A prospective, randomized, double-blind study was conducted to compare FCV dosed at 500 mg and 750 mg tid for 7 days with placebo in the treatment of uncomplicated herpes zoster. 419 immunocompetent patients, aged $\geq 18$ years whose zoster rash had been present for $\leq 72$ hours were enrolled. Patients were assessed for lesion condition and pain pre-therapy, daily during week 1, daily until full crusting during week 2 and then weekly until all crust had been lost. Both FCV doses were equally effective and significantly reduced the duration of VZV recovery from zoster lesions and the time to healing of zoster lesions compared with the placebo-treated group. In addition, a statistically significant decrease in the duration of acute phase pain was detected for famciclovir-treated patients presenting with severe rash when compared with placebo. The effect of famciclovir on PHN (defined as pain at or after healing) was evaluated by assessing pain at 5 monthly visits after healing. The duration of PHN for all age groups was significantly reduced from 128 days to 62 and 55 days following treatment with FCV 500 mg and 750 mg, respectively. There were no significant differences in the safety profiles between famciclovir and placebo. In conclusion, this study demonstrates that famciclovir dosed tid is an effective and well tolerated treatment for patients with acute herpes zoster infection, significantly decreasing the time to cutaneous lesion resolution and the duration of PHN.

The median times to loss of pain following healing in the above study were compared with those seen in a second study (not placebo controlled) for all patients and in patients $\geq 50$ years of age, to confirm that the speed of pain resolutions were of the same order.

| Study | Group | FCV 250 mg | FCV 500 mg | FCV 750 mg | Placebo |
|---|---|---|---|---|---|
| first | All | 56 | 51 | 38 | |
| second | All | | 63 | 61 | 119 |
| first | $\geq 50$ yrs | 56 | 55 | 43 | |
| second | $\geq 50$ yrs | | 63 | 63 | 163 |

These findings therefore further support the conclusions from the placebo-controlled study that famciclovir provides a significant clinical benefit in shortening the duration of post-herpetic neuralgia.

Famciclovir for the Treatment of Acute Herpes Zoster

Effects on Acute Disease and Postherpetic Neuralgia

Authors: Stephen Tyring, MD, PhD,* Rick A. Barbarash, PharmD,† James E. Nahlik, MD,‡ Anthony Cunningham, MBBS, MD,§ John Marley, MD,‖ Madalene Heng, MD,¶ Terry Jones, MD, Ted Rea, MD, Ron Boon, B.Sc. (Hons)., C.Bioi., M.l. Biol., †† Robin Saltzman, MD,†† and The Collaborative Famciclovir Herpes Zoster Study Group.

Authors' Affiliations: *University of Texas Medical Branch, Galveston, Tex. and St. John Hospital, Nassau Bay, Tex.; †St Louis University, St Louis, Mo.; ‡Deaconess Family Medicine, St Louis, Mo.; §Westmead Hospital, Westmead, Australia; ‖University of Adelaide, Adelaide, Australia; ¶VA Medical Center, Sepulveda, Calif.; **Volunteers in Pharmaceutical Research, Bryan Tex.; ††SmithKline Beecham Pharmaceuticals, Brentford, Middlesex, United Kingdom and Philadelphia, Pa.

Corresponding author/Address for reprint requests:
Stephen Tyring, MD, PhD
University of Texas Medical Branch
Center for Clinical Studies
2060 Space Park Drive, Suite 200
Nassau Bay, Tex. 77055
Phone: (713) 333-2288
Fax: (713) 333-2338

Supported by a grant from SmithKline Beecham Pharmaceuticals.

Short Title: Famciclovir: Effects on Acute Zoster and PHN

Number of Words: 3,692

Abstract

Objective: To document the effects of treatment with famciclovir on both the acute signs and symptoms of herpes zoster and postherpetic neuralgia.

Design: A randomized, double-blind, placebo-controlled, multicenter trial.

Setting: Thirty-six centers in the United States, Canada, and Australia.

Patients: Adults (419) with uncomplicated herpes zoster.

Intervention: Patients were randomized within 72 hours after rash onset to receive famciclovir 500 mg, famciclovir 750 mg, or placebo three times daily for seven days.

Measurements: Lesions were assessed daily for up to 14 days until full crusting and then weekly until healing. Viral cultures were obtained daily while vesicles were present. Pain was assessed at each visit at which lesion assessments were made and then monthly for five months following healing. Safety was assessed for the duration of the study.

Results. Famciclovir was well tolerated, with a safety profile comparable with that of placebo. Famciclovir significantly accelerated lesion healing and reduced the duration of viral shedding. Most importantly, patients treated with famciclovir had a significantly more rapid resolution of postherpetic neuralgia (~2-fold faster) when compared with placebo recipients, resulting in about a two month reduction in the median duration of postherpetic neuralgia.

Conclusions. Oral famciclovir 500 mg or 750 mg given three times daily for seven days is an effective and well tolerated treatment for herpes zoster and significantly decreases the duration of the most debilitating complication, postherpetic neuralgia.

Introduction

Herpes zoster (shingles) occurs in 20% of the population and the incidence of the disease increases (three to four times) in the elderly (1). The characteristic zoster rash is often accompanied by significant pain, dysesthesias, and skin hypersensitivity. The unmet challenge in the management of patients with acute zoster is the amelioration of chronic pain. In many patients pain is lost once the affected area of skin returns to normal. However, some patients continue to experience pain long after healing and this is commonly referred to as postherpetic neuralgia. Postherpetic neuralgia is by far the most common complication of herpes zoster infection and is one of the most intractable pain disorders (2,3). The incidence of postherpetic neuralgia rises sharply with increasing age (4,5); nearly half of patients over 60 years of age will suffer from this complication (2,5). Postherpetic neuralgia in older patients is also more severe and persists longer than in younger patients (3), and is clearly the most distressing component of the disease process for both the patient and the physician. Although for many years acyclovir has been the only oral antiviral agent approved for the treatment of patients with acute herpes zoster infections, whether it has an effect on postherpetic neuralgia remains controversial (6–10).

Famciclovir is the well absorbed (77% bioavailable) (11) oral form of penciclovir, a new antiviral agent with activity against varicella-zoster virus (VZV), herpes simplex virus (HSV) types 1 and 2, and Epstein-Barr virus (12–15). The in vitro potency of both penciclovir and acyclovir are dependent on the host cell and assay method used, but are generally comparable (14–16). The 50% plaque inhibitory concentrations ($IC_{50}$) in VZV-infected human lung fibroblasts were 4.0±1.5 mcg/mL and 4.0±1.1 mcg/mL for penciclovir and acyclovir, respectively (14). A potentially clinically important characteristic of penciclovir-triphosphate (PCV-TP) is that it persists in virus-infected host cells longer than acyclovir-triphosphate (ACV-TP) (17). For VZV-infected cells, the intracellular half-life of PCV-TP is 9.1 hours, in contrast to 0.8 hours for ACV-TP (17,18). Thus, PCV-TP has the potential to continue to inhibit viral replication even if serum concentrations are below the inhibitory level. Consistent oral bioavailability linked to a favorable intracellular half-life of PCV-TP in VZV-infected cells suggested that famciclovir could offer clinically important advantages in the management of herpes zoster infections over currently available therapy: a reduced total daily dose and a reduced dosing frequency. Also, there was the expectation that more complete cover of antiviral activity throughout the dosing period could lead to improved clinical efficacy, especially with regard to postherpetic neuralgia. As a result, a study was designed to examine the effects of famciclovir on acute herpes zoster and postherpetic neuralgia.

METHODS

Study Design

This study was a randomized, double-blind, placebo-controlled, multicenter trial to assess the efficacy and safety of famciclovir 500 mg or 750 mg versus placebo, given three times daily for seven days in the treatment of patients with uncomplicated acute herpes zoster infection.

Patients ≧18 years of age with clinically diagnosed uncomplicated herpes zoster infection based on clinical judgment who gave written informed consent were eligible for study entry. Exclusion criteria included patients with zoster rash that had been present for >72 hours; complications of herpes zoster (eg, ocular or visceral involvement, disseminated zoster); presence of crusts at enrollment; patients with other serious underlying disease (eg, immunocompromised and/or HIV-infected individuals); or pregnant or lactating females.

Patients were prohibited from receiving any concomitant antiviral or immunomodifying therapy and any topical medication which would be applied to zoster lesions during the course of the study.

Patient Assessments

Patients were instructed to return to the clinic for lesion and pain evaluations each of the seven therapy days and every day for the next seven days following therapy. Patients with lesions that were fully crusted by day 7 were examined every other day of the week following therapy. After day 14, weekly visits were required of all patients until all lesions had lost their crusts. Patients were assessed for the presence of postherpetic neuralgia at monthly intervals following healing for an additional five months.

The number of papules, vesicles, ulcers, and crusts within the primary dermatome was recorded as none, mild (<25 lesions), moderate (25–50 lesions), or severe (>50 lesions). A specimen for viral culture was taken at baseline and daily thereafter while vesicles were present. Patients were asked to rate the intensity of their pain on a scale of none, mild, moderate, or severe.

Adverse events were assessed at each visit according to time of onset, duration, severity, and investigator defined relationship to study medication. Blood samples were obtained for assessment of chemistry and hematology and urine samples were obtained for dipstick analysis prior to study medication initiation and at the end of therapy visit.

Statistical Analysis

Efficacy endpoints were analyzed by standard survival methods. Analyses employed the Cox proportional-hazards regression model (19). Time-dependent covariates were modeled to evaluate the proportional hazards assumption and a model including the main effects of treatment was employed to examine efficacy. Statistical conclusions were based on the significance of estimated hazard ratios. These were constructed such that values larger than one indicated a faster rate of event occurrence in famciclovir-treated patients than placebo. Two comparisons were made for each endpoint: famciclovir 500 mg versus placebo and famciclovir 750 mg versus placebo. In addition, Kaplan-Meier estimates of the cumulative proportion of patients achieving an event were employed to graphically illustrate the trial results. Proportion data were analyzed by means of Fishers exact test (2-tailed).

The primary efficacy variable was time to full crusting. Secondary variables included duration of viral shedding; time to loss of vesicles, ulcers, crusts, and acute pain; and duration of postherpetic neuralgia (ie, time to loss of pain after healing). Healing was defined as the first visit at which a patient had no papules, vesicles, ulcers, or crusts, and did not develop them at any later visit. Similarly, time to loss of a parameter was the time to complete cessation of that parameter with no further report at any later date. Duration of viral shedding was measured as the number of days from first dose of study medication to the last positive culture.

The pre-study enrollment objective was 300 patients (100 per group). The sample provided 80% power to detect a significant difference from placebo, assuming a true hazard ratio of 1.5 and exponential time to full crusting (or time to event). Data from both the intention-to-treat (patients receiving at least one dose of study medication) and efficacy-evaluable (patients in compliance with the protocol) populations were analyzed. As the results of both analyses were generally comparable, in the current report, data are presented for the intention-to-treat population, unless otherwise specified. Prospectively defined subgroups with respect to age, duration of rash at enrollment, and severity of rash at enrollment were also examined. The safety analysis included all patients who had received at least one dose of study medication. Each analysis included all patients providing information for the respective endpoint. That is, for example, the analysis for time to loss of crusts included all patients who presented with crusts during the study.

RESULTS

Demographics

Characteristics of all randomized patients (n=419) are shown in Table 1, including gender, age, duration of rash, location of rash, severity of rash, and severity of pain. Approximately half of the patients were female. Mean age was 50 years. Over half of the patients had severe rash at enrollment and more than 60% of the patients had moderate or severe zoster pain at enrollment.

Dermatological Assessment

Famciclovir treatment significantly accelerated lesion healing compared with placebo, as demonstrated by shorter times to full crusting, loss of vesicles, loss of ulcers and loss of crusts. In general, the analyses for both the intention-to-treat and the efficacy-evaluable populations were similar and are presented in Table 2.

As noted above, full crusting occurred at a faster rate in patients who received famciclovir compared with those who received placebo. In the intention-to-treat and efficacy-evaluable analyses, the hazard ratios indicate a 1.3–1.5-fold faster time to full crusting for both the famciclovir 500 mg group (hazard ratio: intention-to-treat=1.3; efficacy-evaluable=1.5) and the famciclovir 750 mg group (hazard ratio: intention-to-treat=1.4; efficacy-evaluable=1.5). Statistically significant differences were detected for the famciclovir 500 mg recipients in the efficacy-evaluable analysis (p=0.0245) and for the famciclovir 750 mg recipients in the intention-to-treat and efficacy evaluable analyses (p=0.0228 and 0.0162, respectively).

Virological Assessment

Famciclovir significantly reduced the duration of viral shedding compared with placebo (p=0.0001). At baseline, 58%, 67%, and 70% of patients in the famciclovir 500 mg, famciclovir 750 mg, and placebo groups, respectively, had positive cultures for VZV. The proportion of patients who had stopped shedding virus after one day of treatment was approximately 60% for the famciclovir groups, compared with only 40% in the placebo group.

Acute Pain Assessment

The median times to loss of acute phase pain were 20, 21, and 22 days for the famciclovir 500 mg, famciclovir 750 mg, and placebo groups, respectively. Hazard ratios were 1.2 for the famciclovir 500 mg group and 1.1 for the famciclovir 750 mg group. Although there were no statistically significant differences between the treatment groups in the intention-to-treat population, in the efficacy-evaluable population, patients receiving famciclovir 500 mg lost pain significantly faster than placebo recipients (p=0.0176).

In addition, patients with severe rash (>50 lesions) at enrollment lost pain faster in both the famciclovir 500 mg (intention-to-treat: hazard ratio=1.9; p=0.0028; efficacy-evaluable: hazard ratio=2.9; p=0.0001) and famciclovir 750 mg (intention-to-treat: hazard ratio =1.3; p=0.2143;

efficacy-evaluable: hazard ratio=2.0; p=0.0136) groups. The median days to loss of pain for the famciclovir 500 mg, famciclovir 750 mg, and placebo groups were 20, 27, and 30 days, respectively, in the intention-to-treat population and 20, 27, and 53 days, respectively, in the efficacy-evaluable population. No consistent trends were noted for patients presenting with mild or moderate rash at enrollment.

Postherpetic Neuralgia Assessment

Although there was a comparable proportion of patients who had pain following healing in all treatment groups (52%, 57%, 50% for famciclovir 500 mg, famciclovir 750 mg, and placebo, respectively), both of the famciclovir doses significantly reduced the duration of postherpetic neuralgia in the overall study population (FIG. 1A). Hazard ratios were 1.7 and 1.9 for famciclovir 500 mg and 750 mg, respectively, indicating an almost two-fold reduction in time to postherpetic neuralgia resolution compared with placebo; the reduction in duration of postherpetic neuralgia was statistically significant for both doses of famciclovir (p=0.0202 and 0.0050, respectively). Almost 90% percent of the patients analyzed for loss of postherpetic neuralgia had pain assessments up to month 5. Median days to loss of postherpetic neuralgia were 63, 61, and 119 days for the famciclovir 500 mg, famciclovir 750 mg, and placebo groups, respectively.

In the subgroup of patients most likely to experience postherpetic neuralgia, ie, those $\geq 50$ years of age, postherpetic neuralgia resolved 2.6-times faster in famciclovir recipients than in placebo recipients (p=0.0044 and p=0.0030, for famciclovir 500 mg and 750 mg, respectively; FIG. 1B). Median days to loss of postherpetic neuralgia in these older patients were 63, 63, and 163 days for the famciclovir 500 mg, famciclovir 750 mg, and placebo groups, respectively, representing a reduction in median time of almost 3.5 months for famciclovir recipients. Significant benefit was not detected for the subgroup of patients <50 years of age.

Safety

Famciclovir was well tolerated, with a safety profile similar to that of placebo. The adverse event reported most frequently by the famciclovir 500 mg, famciclovir 750 mg, and placebo recipients was headache (23.2%, 22.2% and 17.8%, respectively) followed by nausea (12.3%, 12.6%, and 11.6%, respectively). For events indicated by the investigator as related to study medication (related, possibly related, unknown or where assessment was missing), once again, the most common adverse events in the famciclovir 500 mg, famciclovir 750 mg and placebo groups were headache (8.0%, 8.1%, and 6.8%, respectively) and nausea (5.1%, 3.0%, and 8.2%, respectively). Famciclovir was not associated with abnormalities in hematology, liver function, clinical chemistry, or urinalysis parameters.

Discussion

Famciclovir given three times daily for seven days demonstrated significant reductions in the acute signs and symptoms of herpes zoster and the duration of viral shedding. Most striking was that the time to cessation of postherpetic neuralgia was significantly reduced in patients who received famciclovir. Famciclovir was well tolerated, with an adverse event incidence comparable with that of placebo. No dose response relationship in efficacy or safety was apparent between the two famciclovir doses.

For many years, acyclovir given 800 mg five times daily for seven to ten days has been the only oral antiviral agent approved for treatment of acute herpes zoster. Its effectiveness in lessening the acute signs and symptoms of herpes zoster has been established (6, 7, 21–23), but "the effects of acyclovir on postherpetic neuralgia are less clear cut." (10)

Postherpetic neuralgia is a common severe complication of herpes zoster. In the largest acyclovir zoster trial (McKendrick et al [8]), no difference was shown between acyclovir and placebo in either the incidence or the duration of postherpetic neuralgia, despite enrolling only those patients most at risk of developing postherpetic neuralgia (eg, elderly). However, in two smaller trials (Huff et al [7]; Morton and Thompson [24]) which enrolled both young and elderly patients in about equal proportions, some effects were seen during the first three months, but not during months 4 to 6. When one of these studies was re-analyzed (Huff et al [9]), a significant effect was seen on all zoster-associated pain (ie, continuum of pain from enrollment into study until complete cessation), but postherpetic neuralgia was not addressed.

Additionally, a recent study evaluating acyclovir administered for 7 or 21 days with or without concomitant prednisolone for the treatment of acute herpes zoster revealed that although acute pain was reduced in patients treated with concomitant prednisolone or 21 days of acyclovir compared with those who had received 7 days of acyclovir treatment alone, neither the frequency of zoster-associated pain nor the time to complete cessation of pain was affected by the 14 additional days of acyclovir treatment or by concomitant prednisolone therapy (10). No information on the duration of postherpetic neuralgia was reported from that study. Also, as this study did not include a placebo control, no conclusion can be drawn regarding the effect of acyclovir on postherpetic neuralgia.

Postherpetic neuralgia has been defined in relationship to acute zoster onset (6–8, 24), at time points ranging from one to six months after zoster rash appears, and in relationship to healing of zoster lesions (25, 26), as was done in the current study. Since the definition of postherpetic neuralgia varies between studies, comparability of patient populations may be shown by examining the prevalence of pain in the placebo-treated groups persisting six months after zoster rash onset. In the current study, 18.5% of the placebo recipients reported pain six months after rash onset; this value is in agreement with the prevalence of pain reported by placebo recipients in other published studies (6, 8, 24).

In this study, famciclovir clearly demonstrated a significant reduction in the duration of postherpetic neuralgia in comparison with placebo. Important features of the current study include prospectively defined postherpetic neuralgia, the duration of follow-up (almost 90% of patients in the postherpetic neuralgia analysis were assessed five months after healing), and reliance on rigorous statistical methodology to evaluate the duration of postherpetic neuralgia. The present report summarizes postherpetic neuralgia over the entire follow-up period (five months after healing) in a single statistic (ie, the hazard ratio). Additionally, the loss of pain was identified as the time at which the patients reported no zoster related pain and, most importantly, they were continued in the study and never reported pain again for the remainder of the study period. Thus, the value of two for an estimated hazard ratio, indicates that the event of interest occurs twice as rapidly in patients receiving famciclovir than in controls. Patients receiving famciclovir during acute zoster lost postherpetic neuralgia almost two times faster than those receiving placebo (500 mg: hazard ratio=1.7, p=0.0202; 750 mg: hazard ratio=1.9, p=0.0050). In older patients (L$\geq$50 years of age), who are more at risk and in whom postherpetic neuralgia persists longer, those who were treated with famciclovir during acute zoster lost pain 2.6-times faster than those who received placebo (500 mg: p=0.0044; 750 mg: p=0.0030), resulting in a 3.5-month reduction in median duration of postherpetic neuralgia.

In conclusion, oral famciclovir 500 mg or 750 mg administered three times daily for seven days during acute zoster offers significant benefit to patients with herpes zoster by providing a well tolerated convenient dosage regimen, effective relief of acute zoster signs and symptoms, and shortening the duration of postherpetic neuralgia.

The Collaborative Famciclovir Herpes Zoster Study Group

Baylor College of Medicine, Houston, Tex.: Suzanne Bruce, MD, Annette Harris, MD, Anne Epstein, MD, Lisa Lowry, MD, Howard Rubin, MD, John Dupuy, MD, Jay Hendricks, MD, Jeanette Greer, MD; Beverly Hills, Calif.: Marvin Rapaport, MD; Bucks County Clinical Research, Morrisville, Pa.: David J Miller, DO, Brad S Friedmann, DO, Randi M Silverbrook, DO, Wayne Marley, MD; Clinical Study Center, Fort Myers, Fla./ Cape Coral, Fla: Stephen R Zellner, MD, David D Michie, PhD, Felix Mestas, MD, Ronica Kluge, MD, Quinnon R Purvis, MD, Nancy Schleider, MD, Juan Domingo, MD; Colorado Medical Research Center, Denver, Colo.: James M Swinehart, MD, Kathy Williams, RN, Lisa Shultz, RN, Bonnie Rochambeaum LPN; Deaconess Family Medicine/Old Orchard Geriatrics & Family Medicine/Southside Family Practice/ Spurgeon Medical Group/St. Louis Medical Research, St. Louis, Mo.: James Nahlik, MD, Rick A Barbarash, PharmD, David Campbell, MD, James Price, MD, Mark King, MD, Percival Moraleda, MD, Michael Toro, MD, Marta Mortensen, MD, Melinda Walker, MD, Bryan Steele, MD, Kathleen Castellanos, MD, M Dale Terrel, MD, Jessee Crane, MD; Robert Zink, MD, Scott Soerries, MD, Charles Nester, MD, Stephen Nester, MD, Glennon Fox, MD, Charles Crecelius, MD, Morton Singer, MD, Linda Stanton, MD; George Washington University Medical Center, Washington, D.C.: Mervyn L Elgart, MD, Gayle Masri-Fridling, MD, Michael Noonan, MD, Pamela Scheinman, MD, M Carol McNeely, MD, Maria Turner, MD; Georgetown University Medical Center, Washington, D.C.: Virginia I Sulica, MD; Georgia Clinical Research Center, Atlanta, Ga.: Stephen J Kraus, MD, Edmond I Griffin, MD, D Scott Karempelis, MD, Bette C Potter, MD, Diane M Smith, LPN; Harborview Medical Center, Seattle, Wash.: Lawrence Corey, MD, Thomas Gill, MD; Henry Ford Hospital, Detroit, Mich.: Orlando G Rodman, MD, Robert Norum, MD, Dennis Babel, PhD; Le Centre Hosptitalier de l'Universite Laval, Ste. Foy, Quebec, Canada: Alain Martel, MD; LSU School of Medicine/Charity Hospital of Louisiana at New Orleans/LSU Lions Clinic, New Orleans, La.: Lee T Nesbitt, Jr. MD, Brian D Lee, MD, Donna G Heitler, MD, Eric Hollabaugh, MD; Maplewood Family Practice/ Piedmont Research Associates, Winston-Salem, N.C.: John BR Thomas, MD, Sherrill D Braswell, Jr., MD, John G Roach III, MD, Richard C Worf, MD, Champ M Jones, MD, Thomas B Cannon, MD, Thomas W Littlejohn, III, MD, Keith V VanZandt, MD, Gina Gottesman Shar, MS; Melbourne, Australia: Andrew Hellyar, MBBS; Minnesota Clinical Study Center, Fridley, Minn.: H Irving Katz, MD, Steven E Prawer, MD, Jane S Lindholm, MD, Ngo T Hien, MD, Frederick S Fish, MD, Jack C Scott, MD, Steven Kempers, MD, M Elizabeth Briden, MD; Montreal, Quebec, Canada: Michel Lassonde, MD, Claude Girard, MD; Montreal, Quebec, Canada: Victor Oliel, MD; Mt. Sinai Hospital, Toronto, Ontario, Canada: Andrew Simor MD, D Low, MD, H Velland, MD, W Gold, MD; Nalle Clinic/ Metrolina/Nalle Clinic, Charlotte, N.C.: John L Benedum, MD, Ophelia E Garmon-Brown, MD, WS Tucker, Jr., MD, Kim Tam, MD, Ed Landis, MD, C. Whit Blount, MD, Selwyn Spangenthal, MD, Geoffrey Chapman, MD; Palm Beach Center for Clinical Investigation, W Palm Beach, Fla.: Lee Fischer, MD, Holly W. Hadley, MD; St. Joseph's Health Centre of London, London, Ontario, Canada: Daniel Gregson, MD, Ole Hammerberg, MD; St. Michael's Hospital Toronto, Ontario, Canada: Ignatius Fong, MD; SIU School of Medicine, Memorial Medical Center, St. John's Hospital, Springfield, Ill.: Larry A Von Behren, MD, Sergio Rabinovich, MD, Nancy Khardori, MD; SmithKline Beecham Pharmaceuticals, Philadelphia, Pa., USA, Brentford, Middlesex, UK, Melbourne, Australia, and Oakville, Ontario, Canada: Robin Saltzman, MD, Ron Boon, B.Sc. (Hons)., C.Biol., M.l.Biol., David Fitts, PhD, Charles Grier, PhD, David Griffin, PhD, Duncan McKay, Richard Birkenmaier, Simon Bishop, G. Lynn Marks, MD, Leslie Locke, PhD, Regina Jurewicz, RPh, Susan Weill, BSN, Thomas Mayewski, Carol Frazier, Ann Grossman, James MacDonald, Pam Murphy, Kathryn Stiede, Mary Beth Weigart, Mary Levidiotis, Marilyn Hosang, Jim Parsons; Sunnybrook Medical Centre, Toronto, Ontario, Canada: Anita R. Rachlis, MD; Toronto, Ontario, Canada: Gary D Schachter, MD, Ricky K Schachter, MD; University of Adelaide, Adelaide, South Australia: John Marley, MD, David Gordon, MD, Peter Hallsworth, PhD, Diane Markham, RN, Elizabeth Wilkinson, RN, M Geraldine Smith, RN; University of Arizona Health Sciences Center, Tucson, Ariz.: Kevin Welch, MD; University of California, San Diego School of Medicine/VA Medical Center, San Diego, Calif.: Daniel Piacquadio, MD, Ann Fleming, RN; University of Cincinnati, Cincinnati, Ohio: Debra L Breneman, MD, Bhakta V Chetty, MD, Steven Manders, MD, Boris Lushniak, MD; University of Miami, Miami, Fla: Daniel Hogan, MD; University of Newcastle, Callaghan, New South Wales, Australia: Alexander Reid, MD, G Tannock, MD, Nannette Dick, RN, Loma Crossley, RN; University of Texas Medical Branch, Galveston, Tex: Stephen K. Tyring, MD, PhD, Robert Purvis, MD, Dayna Diven, MD, Neill Porter, MD; University of Texas Medical School at Houston, Houston, Tex.: Adelaide A Hebert, MD, John Bradford Bowden, MD Keith Edward Schulze, MD; University Hospital, Saskatoon, Saskatchewan, Canada: Kurt E Williams, MD, JM Conly, MD, C Anderson, MD; VA Medical Center, Minneapolis, Minn.: Janellen Smith, MD, Nancy Krywonis, MD; VA Medical Center, Sepulveda, Calif.: Madalene CY Heng, MD; Volunteers In Pharmaceutical Research, Bryan, Tex.: Ted L Rea, MD, Terry Jones, MD; Wenatchee Valley Clinic, Wenatchee, Wash.: Richard Tucker, MD, Byron W Lee, MD, Cooky Ogle; Westlake Village, Calif./ Simi Valley, Calif.: James S Weintraub, MD; Westmead Hospital, Westmead, Australia: A. Cunningham, MBBS, MD, Dominic Dwyer, MBBS, David Holland, MBBS, Margaret Fordham, RN, Graeme Miller, MBBS, Terina Sylvester, RN; West Paces Ferry Hospital, Atlanta, Ga.: Steven I Marlowe, MD, Mark L Tanner, MD; Wheatridge, Colo.: Pasquale A DiLorenzo, MD.

References

1. Gelb L D. Varicella zoster virus infections. Curr Opin Infect Dis. 1989;2:256–61.

2. Portenoy R K, Duma C, Foley K M. Acute herpetic and postherpetic neuralgia: clinical review and current management. Ann Neurol. 1986;20:651–64.

3. Loeser J D. Herpes zoster and postherpetic neuralgia. Pain. 1986;25:149–64.

4. Strommen G L, Pucino F, Tight R R, Beck C l. Human infection with herpes zoster: Etiology, pathophysiology, diagnosis, clinical course, and treatment. Pharmacotherapy. 1989;8:52–68.

5. Demoragas J M, Kierland R R. The outcome of patients with herpes zoster. Arch Dermatol. 1957;75:193–6.

6. Wood M J, Ogan P H, McKendrick M W, Care C D, McGill J I, Webb E M. Efficacy of oral acyclovir treatment of acute herpes zoster. Am J Med. 1988;85 (Suppl 2A):79–83.

7. Huff J C, Bean B, Balfour H H, Laskin O L, Connor J D, Corey L, et al. Therapy of herpes zoster with oral acyclovir. Am J Med. 1988;85 (Suppl 2A):84–9.

8. McKendrick M W, McGill J I, Wood M J Lack of effect of acyclovir on postherpetic neuralgia. Br Med J. 1989;298:431.

9. Huff J C, Drucker J L, Clemmer A, Laskin O L, Connor J D, Bryson Y J, et al. Effect of oral acyclovir on pain resolution in herpes zoster: A reanalysis. J Med Virol. 1993;1 (Suppl 1):93–6.

10. Wood M J, Johnson R W, McKendrick M W, Taylor J, Mandal B K, Crooks, J. A randomized trial of acyclovir for 7 days or 21 days with and without prednisolone for treatment of acute herpes zoster. New Engl J Med. 1994;330:896–900.

11. Pue M, Benet L Z Pharmacokinetics of famciclovir in man. Antiviral Chem Chemother. 1993;4(Suppl):47–55.

12. Boyd M R, Bacon T H, Sutton D, Cole M. Antiherpesvirus activity of 9-(4-hydroxy-3-hydroxy-methylbut-1-yl) guanine (BRL 39123) in cell culture. Antimicrob Agents Chemother. 1987;31:1238–1242.

13. Boyd M R, Boon R J, Fowles S E, Pagano K, Prince W T, Sutton D, et al. Some biological properties of BRL 42810, a well-absorbed oral prodrug of the anti-herpesvirus agent BRL 39123. Antiviral Res. 1988;9:146.

14. Boyd M R, Safrin S, Kern E R. Penciclovir a review of spectrum of activity, selectivity, and cross-resistance pattern. Antiviral Chem Chemother. 1993;4(Suppl):3–11.

15. Bacon T, Schinazi R. An overview of the further evaluation of penciclovir against herpes simplex virus and varicella-zoster virus in cell culture, highlighting contrasts with acyclovir. Antiviral Chem Chemother. 1993;4(Suppl) :25–36.

16. DeClerq E. Comparative efficacy of antiherpes drugs in different cell lines. Antimicrob Agents Chemother. 1982;21:661–3.

17. Earnshaw D L, Bacon T H, Darlison S J, Edmunds K, Perkins R M, Vere Hodge R A. Mode of antiviral action of penciclovir in MRC-5 cells infected with herpes simplex virus. Antimicrob Agents Chemother. 1992;36:2747–57.

18. Standring-Cox R, Bacon T H, Howard B, Gilbart J, Boyd M R. Prolonged activity of penciclovir against varicella-zoster virus in cell culture [Abstract]. In: Program and Abstracts of the 7th International Conference on Antiviral Research. Charleston, S.C.; 1994:114.

19. Cox D R. Regression models and life tables (with discussion). J Royal Stat Soc, Series B. 1972;34:187–220.

20. Hochberg Y. A sharper Bonferroni procedure for multiple tests of significance. Biometika. 1988;75(4):800–2.

21. McKendrick M W, McGill J I, White J E, Wood M J. Oral acyclovir in acute herpes zoster. Br Med J. 1986;293:1529–32.

22. Wood M J, McKendrick M W, McGill J I. Oral acyclovir for acute herpes zoster infections in immunecompetent adults. Infection. 1987;15(Suppl 1):S9–13.

23. Sasadeusz J J, Sacks S L. Systemic antivirals in herpesvirus infections. Derm Clinics. 1993;11:171–85.

24. Morton P, Thompson A N. Oral acyclovir in the treatment of herpes zoster in general practice. N Z Med J. 1989;102:93–5.

25. Cobo M L, Foulks G N, Liesegang T, Lass J, Sutphin J E, Wilhelmus K, et al. Oral acyclovir in the treatment of acute herpes zoster ophthalmicus. Ophthalmology. 1986;93 (6):763–70.

26. Watson P N, Evans R J. Postherpetic neuralgia: A review. Arch Neurol. 1986;43:836–40.

TABLE 1

Patient Characteristics at Study Enrollment

| | Famciclovir 500 mg | Famciclovir 750 mg | Placebo |
|---|---|---|---|
| No. of Patients | 138 | 135 | 146 |
| % Female/Male | 45.7/54.3 | 48.9/51.1 | 47.3/52.7 |
| Mean Age (years) | 50.1 | 49.5 | 49.1 |
| <50 years (%) | 49.3 | 48.9 | 52.1 |
| ≥50 years (%) | 50.7 | 51.1 | 47.9 |
| Duration of Rash (%) | | | |
| <48 hours | 47.8 | 56.3 | 49.3 |
| 48–72 hours | 51.5* | 43.7 | 50.7 |
| Location of Rash (%) | | | |
| Thoracic | 50.0 | 56.3 | 54.8 |
| Cervical | 25.4 | 18.5 | 26.0 |
| Lumbar | 14.5 | 13.3 | 13.7 |
| Cranial | 5.1 | 7.4 | 4.1 |
| Sacral | 5.1 | 4.4 | 1.4 |
| Severity of Rash (%) | | | |
| No lesions | — | — | 0.7 |
| Mild | 21.0 | 25.9 | 23.3 |
| Moderate | 22.5 | 20.7 | 24.7 |
| Severe | 56.5 | 53.3 | 51.4 |
| Severity of Pain (%) | | | |
| None | 5.8 | 5.9 | 8.2 |
| Mild | 24.1 | 28.9 | 33.6 |
| Moderate | 36.5 | 34.1 | 30.8 |
| Severe | 32.8 | 31.1 | 27.4 |

*One patient (0.7%) enrolled at 77 hours after rash onset.

TABLE 2

Cutaneous Lesion Resolution*

| | Famciclovir 500 mg | Famciclovir 750 mg | Placebo |
|---|---|---|---|
| Time to Full Crusting | | | |
| N | 119 (91) | 120 (92) | 133 (101) |
| Median [days] | 5 (6) | 6 (8) | 7 (7) |
| Hazard ratio | 1.3 (1.5) | 1.4 (1.5) | |
| 95% C.I. | 1.0–1.7 (1.1–2.0) | 1.0–1.9 (1.1–2.1) | |
| p value† | 0.0995 (0.00245) | 0.0228 (0.0162) | |
| Time to Loss of Vesicles | | | |
| N | 133 (104) | 131 (103) | 143 (110) |
| Median [days] | 5 (5) | 5 (5) | 6 (6) |
| Hazard ratio | 1.4 (1.6) | 1.7 (2.0) | |
| 95% C.I. | 1.1–1.9 (1.2–2.2) | 1.3–2.2 (1.4–2.7) | |
| p value† | 0.0129 (0.0024) | 0.0004 (0.0001) | |

TABLE 2-continued

Cutaneous Lesion Resolution*

|  | Famciclovir 500 mg | Famciclovir 750 mg | Placebo |
|---|---|---|---|
| Time to Loss of Ulcers | | | |
| N | 72 (55) | 73 (59) | 89 (70) |
| Median [days] | 7 (7) | 7 (7) | 9 (10) |
| Hazard ratio | 1.6 (1.7) | 1.6 (1.7) | |
| 95% C.I. | 1.1–2.2 (1.2–2.5) | 1.1–2.2 (1.2–2.5) | |
| p value† | 0.0119 (0.0064) | 0.0087 (0.0065) | |
| Time to Loss of Crusts | | | |
| N | 129 (103) | 126(101) | 142 (112) |
| Median [days] | 19 (19) | 20 (20) | 21 (21) |
| Hazard ratio | 1.3 (1.5) | 1.2 (1.2) | |
| 95% C.I. | 1.0–1.7 (1.1–2.0) | 0.9–1.6 (0.9–1.6) | |
| p value† | 0.0476‡ (0.0092) | 0.1926 (0.2185) | |

*Analyses for the intention-to-treat and efficacy-evaluable (displayed in parentheses) populations
†Famciclovir dose compared with placebo
‡Not statistically significant after adjusting for multiple comparisons (20)

We claim:

1. A method for the treatment of PHN in mammals, which method comprises administrating to the mammal in need of such treatment, an effective amount of famciclovir or penciclovir, or a pharmaceutically acceptable salt thereof.

2. A method according to claim 1 wherein the treatment is within 72 hours of rash onset.

3. A method according to claim 2 wherein the treatment is within 48 hours of rash onset.

4. A method according to claim 1 where the treatment period is 7 days.

5. A method according to claim 1 wherein the treatment is carried out on patients of greater than 50 years of age.

6. A method according to claim 5 wherein the treatment is carried out on patients of greater than 60 years of age.

7. A method according to claim 6 wherein the treatment is carried out on patients of greater than 70 years of age.

8. A method according to claim 1 wherein the compound is famciclovir.

9. A method according to claim 8 wherein famciclovir is administered at a dose of 250 mg, 500 mg or 750 mg, once, twice or three times a day.

10. A method according to claim 9 wherein famciclovir is administered at a dose of 250 mg three times a day.

11. A method according to claim 9 wherein famciclovir is administered at a dose of 500 mg three times a day.

12. A method according to claim 9 wherein famciclovir is administered at a dose of 500 mg twice a day.

13. A method according to claim 9 wherein famciclovir is administered at a dose of 750 mg once a day.

14. A method according to claim 1 wherein the mammal is a human.

15. A method for the prophylactic treatment of PHN in a human in need of such treatment, which method comprises administrating to said human, an effective prophylactic amount of famciclovir or penciclovir, or a pharmaceutically acceptable salt thereof.

16. A method according to claim 15 wherein the compound is famciclovir.

17. A method according to claim 16 wherein famciclovir is administered at a dose of 250 mg, 500 mg or 750 mg, once, twice or three times a day.

18. A method according to claim 17 wherein famciclovir is administered at a dose of 250 mg three times a day.

19. A method according to claim 15 wherein the treatment is carried out on patients of greater than 50 years of age.

20. A method according to claim 19 wherein the treatment is carried out on patients of greater than 60 years of age.

21. A method according to claim 20 wherein the treatment is carried out on patients of greater than 70 years of age.

* * * * *